United States Patent
Hendriks et al.

(10) Patent No.: US 9,131,845 B2
(45) Date of Patent: Sep. 15, 2015

(54) OPTICAL PROBE

(75) Inventors: Bernardus Hendrikus Wilhelmus Hendriks, Eindhoven (NL); Gert T Hooft, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 473 days.

(21) Appl. No.: 12/810,872

(22) PCT Filed: Dec. 19, 2008

(86) PCT No.: PCT/IB2008/055460
§ 371 (c)(1),
(2), (4) Date: Jun. 28, 2010

(87) PCT Pub. No.: WO2009/087522
PCT Pub. Date: Jul. 16, 2009

(65) Prior Publication Data
US 2010/0288912 A1    Nov. 18, 2010

(30) Foreign Application Priority Data

Jan. 4, 2008 (EP) .................................... 08100105
May 28, 2008 (EP) .................................... 08157034

(51) Int. Cl.
*G01J 1/04* (2006.01)
*G01J 1/42* (2006.01)
(Continued)

(52) U.S. Cl.
CPC ........... *A61B 5/0062* (2013.01); *A61B 1/00096* (2013.01); *A61B 1/00165* (2013.01); *A61B 1/00183* (2013.01); *A61B 5/0084* (2013.01); *A61B 5/0068* (2013.01); *A61B 5/0075* (2013.01)

(58) Field of Classification Search
CPC .. A61B 10/00; A61B 1/00009; A61B 3/1025; A61B 1/00057; A61B 1/00163; A61B 5/0068; A61B 1/002; A61B 1/06; G02B 21/002; G02B 21/0024; G02B 23/24; G02B 21/0028
USPC ...................... 250/208.2, 216, 227.11, 208.1; 385/31–35, 14, 15, 117; 348/45, 65, 348/72; 600/101
See application file for complete search history.

(56) References Cited

U.S. PATENT DOCUMENTS 5,305,759 A    4/1994  Kaneko
6,485,413 B1 *  11/2002  Boppart et al. ............... 600/160
(Continued)

FOREIGN PATENT DOCUMENTS

JP    04-135550     5/1992
JP    2002236223 A  2/2001
(Continued)

OTHER PUBLICATIONS

Johnston et al. "Optical modeling of an ultrathin scanning fiber endoscope, a preliminary study of confocal versus non-confocal detection", Sep. 19, 2005, vol. 13, No. 19, Optics Express pp. 7548-7562.*
(Continued)

*Primary Examiner* — Francis M Legasse, Jr.

(57) ABSTRACT

The invention relates an optical probe (1) suitable for non-linear optics such as two-photon imaging for medical purposes. The probe has an optical guide (2) and a lens system (6) positioned rigidly at an end portion (2*a*) of the optical guide. Additionally, a housing (3) with a cavity for the optical guide (2) and the lens system (6), the housing having at its distal end a transparent window (4), is comprised in the probe. The optical guide (2) with the lens system (6) is displaceably mounted within the housing, preferably in a transverse direction. Also, the housing (3) has an auxiliary, peripheral optical guide (5) optically connected to the transparent window (4). The invention is advantageous for obtaining an optical probe with a significantly larger collection efficiency. The optical probe may advantageous be applied in connection with two-photon spectroscopy where both ballisitic photons and diffusing fluorescence photons can be used in the detection of an event.

16 Claims, 4 Drawing Sheets

(51) Int. Cl.
*G01J 5/08* (2006.01)
*A61B 5/00* (2006.01)
*A61B 1/00* (2006.01)

(56) References Cited

U.S. PATENT DOCUMENTS

| | | | |
|---|---|---|---|
| 7,391,013 B2 | 6/2008 | Johnston et al. | |
| 8,029,438 B2 * | 10/2011 | Hagihara et al. | 600/169 |
| 8,289,522 B2 | 10/2012 | Tearney | |
| 2001/0055462 A1 | 12/2001 | Seibel | |
| 2003/0086161 A1 * | 5/2003 | Harris | 359/368 |
| 2003/0191397 A1 * | 10/2003 | Webb | 600/476 |
| 2004/0156124 A1 * | 8/2004 | Okada | 359/754 |
| 2006/0158655 A1 | 7/2006 | Everett et al. | |
| 2007/0025662 A1 * | 2/2007 | Gugel | 385/39 |
| 2007/0038123 A1 | 2/2007 | Fulghum | |
| 2007/0236782 A1 | 10/2007 | Sano | |

FOREIGN PATENT DOCUMENTS

| | | | |
|---|---|---|---|
| JP | 2004305586 | 4/2003 | |
| JP | 2004159924 A | 6/2004 | |
| WO | WO 2007063658 A1 * | 6/2007 | A61B 1/00 |

OTHER PUBLICATIONS

Palero et al., "In Vivo Intrinsic Emission Spectral Imaging Microscopy of Mouse Skin Tissues", SPIE, vol. 6089, 2006, pp. 1A1-1A11.

Fu et al., "Nonlinear Optical Microscopy Based on Double-Clad Photonic Crystal Fibers", Optics Express 13, 2005, 5528-5534.

Seibel et al., "A Full-Color Scanning Fiber Endoscope", Optical Fibers and Sensors for Medical Diagnostics and Treatment Applications VI, Proc. SPIE, vol. 6083, 2006, pp. 608303-1-608303-8.

* cited by examiner

OPTICAL PROBE

CROSS REFERENCE TO RELATED APPLICATION

Related application is PCT serial no. IB2008/055483, U.S. patent Ser. No. 12/810,523, "An Optical Probe," filed Dec. 22, 2008.

FIELD OF THE INVENTION

The present invention relates to an optical probe suitable for miniature applications, e.g. in-vivo medical inspections and procedures or in industrial inspections, for instance inspection of food or small devices. The invention also relates to a corresponding imaging system and a method for imaging with such an imaging system.

BACKGROUND OF THE INVENTION

For correct diagnosis of various diseases, e.g. cancer, biopsies are often taken. This can either be via a lumen of an endoscope or via needle biopsies. In order to find the correct position to take the biopsy, various imaging modalities are used such as X-ray, MRI and ultrasound. In case of e.g. prostate cancer in most cases the biopsy is guided by ultrasound. Although helpful, these methods of guidance are far from optimal. The resolution is limited and, furthermore, these imaging modalities can in most cases not discriminate between benign and malignant tissue. As a result a physician does not know for certain that from the correct part of the tissue a biopsy is taken. Thus, the physician takes almost blind biopsies and even if after inspection of the tissue no cancer cells are detected, one does not know for certain that simply the right spot to take the biopsy was missed.

In order to improve the biopsy procedure direct inspection of the biopsy position prior of taken the biopsy is required. A way to achieve this is by microscopic inspection at this position. This requires a miniaturised confocal microscope. For even more detailed tissue inspection non-linear optical techniques allow high molecular contrast without the need of staining the tissue (see J. Palero et al. SPIE vol. 6089 (2006) pp. 1A1-1A11). These techniques are based on two-photon and second harmonic spectral imaging. In order to make the scanner compatible with these non-linear techniques photonic crystal fibers should be employed with large core diameters in order to reduce non-linear effects in the optical fiber itself. Nevertheless, the collection efficiency for two-photon imaging or other non-linear optical techniques may be low. One way of increasing the collection may be to increase the solid angle extended by the optical fiber. L. Fu, X. Gan and M. Gu, in "Nonlinear optical spectroscopy based on double-clad photonic crystal fibers", Optics Express 13 (2005) 5528, for example shows how to increase collection efficiency significantly by exploiting the inner cladding and the core of the double-clad photonic crystal fiber (PCF). However, the resulting numerical aperture is still rather low for practical applications.

Hence, an improved optical probe would be advantageous, and in particular a more efficient and/or reliable optical probe would be advantageous.

SUMMARY OF THE INVENTION

Accordingly, the invention preferably seeks to mitigate, alleviate or eliminate one or more of the above mentioned disadvantages singly or in any combination. In particular, it may be seen as an object of the present invention to provide an optical probe that solves the above mentioned problems of the prior art with the collection efficiency.

This object and several other objects are obtained in a first aspect of the invention by providing an optical probe, the probe comprising:
an optical guide,
lens system positioned rigidly at an end portion of the optical guide,
a housing with a cavity for the optical guide and the lens system, the housing having at its distal end a transparent window,
wherein the optical guide with the lens system is displaceably mounted within the housing, and
wherein the housing further comprises an auxiliary, peripheral optical guide optically connected to the transparent window.

The invention is particularly, but not exclusively, advantageous for obtaining an optical probe with a significantly larger collection efficiency. The optical probe may advantageously be applied in connection with two-photon spectroscopy where both ballisitic photons and diffusing fluorescence photons can be used in the detection of an event. Furthermore, the optical probe according to the present invention may be beneficially applied for detection of scattered radiation for both linear and non-linear spectroscopy.

In the context of the present invention it is to be understood that the term "optical guide" may include, and is not limited to, optical fibers (multi-mode and single-mode), thin film optical paths, photonic crystal fibers, photonic bandgab fibers (PBG), polarization maintaining fibers, etc. The optical probe may also comprise more than one fiber i.e. a plurality of fibers or a fiber bundle.

It could be mentioned that a scanning fiber endoscope with a ring of optical fibers used for collecting light from a central, displaceable optical fiber is disclosed in Eric J. Seibel et al., Optical Fibers and Sensors for Medical Diagnostics and Treatment Applications VI, Proc. SPIE, Vol. 6083, 608303, (2006). However, the central fiber of the endoscope does not have a lens system attached thereto and consequently the effective numerical aperture is not sufficiently high for e.g. non-linear optical imaging. The two-photon imaging setup briefly mentioned in the work of Seibel et al. is not workable with the endoscope configuration shown in FIG. 2 of that reference, and it is not completely clear how this two-photon imaging is performed.

Beneficially, the optical guide and the lens system may be arranged for confocal imaging. Alternatively or additionally, the auxiliary, peripheral optical guide may be arranged for non-confocal imaging. For instance the guide may be arranged for collecting diffusive photons that are scattered multiple times. Thus, the auxiliary, peripheral optical guide may typically be arranged for receiving reflected light emitted by the optical probe.

Advantageously, the auxiliary, peripheral optical guide may extend substantially along at least half the periphery of the end part of the optical probe. Typically the guide may extend the entire periphery, but it could also be less. The shape is depending on the optical probe and its housing but typically a cross-sectional section may be substantially circular, in cross-section, but not necessarily. Thus, various forms and shapes of the peripheral guide are readily envisioned.

Typically, the optical guide may be an optical fiber, and the lens system may be positioned a distance (L) away from the optical exit of the optical fiber, the distance (L) being significantly larger than a core diameter of the optical fiber. The ratio between the distance (L) and the fiber diameter at an exit position may be 5, 10, 20, or 30, and even more. Additionally, or alternatively, the lens system may be rigidly connected to the optical guide with an intermediate mount fixated at the distal end of the optical guide and fixated on the lens system.

Preferably, the lens system at the distal end of the optical guide may be mounted displaceable in a transverse direction of the optical guide in order to enhance the field of view (FOV). It may be elastically mounted.

The transparent windows of the housing may comprise a further lens system, the further lens system being rigidly connected or fixed to the housing.

Preferably, the cross-sectional area of the auxiliary, peripheral optical guide may be substantially unchanged along the optical probe. This to obtain etendue conservation, but the shape may change depending on the shape of probe and detector exit.

For some applications, the lens system may have a numerical aperture so as to enable non-linear optical phenomena, e.g. two photons events and frequency mixing as described more detailed below. A numerical aperture of at least 0.3, or at least 0.4, or at least 0.5, or at least 0.6, may make it easier to perform non-linear optics.

For non-linear applications, the optical guide may be a single-mode optical fiber. Alternatively or additionally, the optical guide may be a photonic crystal fiber, or a polarization maintaining fiber because these kind of optical guide has several advantageous optical properties that are especially beneficial to exploit in the context of the present invention.

For some applications, the optical probe may form part of an endoscope, a catheter, a needle, a biopsy needle, or other similar application as the skilled person will readily realized. It is also contemplated that fields of application of the present invention may include, but is not limited to, fields where small imaging devices are useful, such as in industries using inspection with small-scale devices etc.

In a second aspect, the present invention relates to an optical imaging system, the system comprising
   an optical probe according to the first aspect,
   a radiation source optically coupled to said optical probe, the probe being arranged for guiding radiation emitted from the radiation source to a region of interest (ROI), and
   an imaging detector optically coupled to said optical probe, the detector being arranged for imaging using reflected radiation from the region of interest (ROI).

In the context of the present invention it is to be understood that the term "radiation source" may comprise any suitable kind of radiation source including, and not limited to, lasers (of any wavelength and any mode of operation i.e. continuous or pulsed of any period incl. femto seconds laser), LEDs, gas-discharge lamps, any kind of luminescence, etc.

Preferably, the radiation source of the optical imaging system may be capable of emitting radiation with an intensity, and/or with a spatial and temporal distribution so at to enable non-linear optical phenomena, e.g. two photon imaging and frequency mixing.

Thus, the system may be a two photon imaging system, or a second harmonic generation (SHG) imaging or third or higher order harmonic generation. Preferably, the radiation source is a laser source with a femto-second (fs) pulsed laser. The imaging system may then comprise appropriate dispersion compensating means. The imaging system may however also perform more linear optical imaging e.g. the imaging system may be a fluorescence imaging system, etc.

In a third aspect, the present invention relates to a method for optical imaging, the method comprising:
   providing an optical probe according to the first aspect,
   providing a radiation source (IS) which is optically coupled to said optical probe, the probe being arranged for guiding radiation emitted from the radiation source to a region of interest (ROI), and
   performing an imaging process with an imaging detector (ID) optically coupled to said optical probe, the detector being arranged for imaging using reflected radiation from the region of interest (ROI).

The first, second and third aspect of the present invention may each be combined with any of the other aspects. These and other aspects of the invention will be apparent from and elucidated with reference to the embodiments described hereinafter.

BRIEF DESCRIPTION OF THE DRAWINGS

The present invention will now be explained, by way of example only, with reference to the accompanying Figures, where.

DETAILED DESCRIPTION OF EMBODIMENTS

Figure 1:
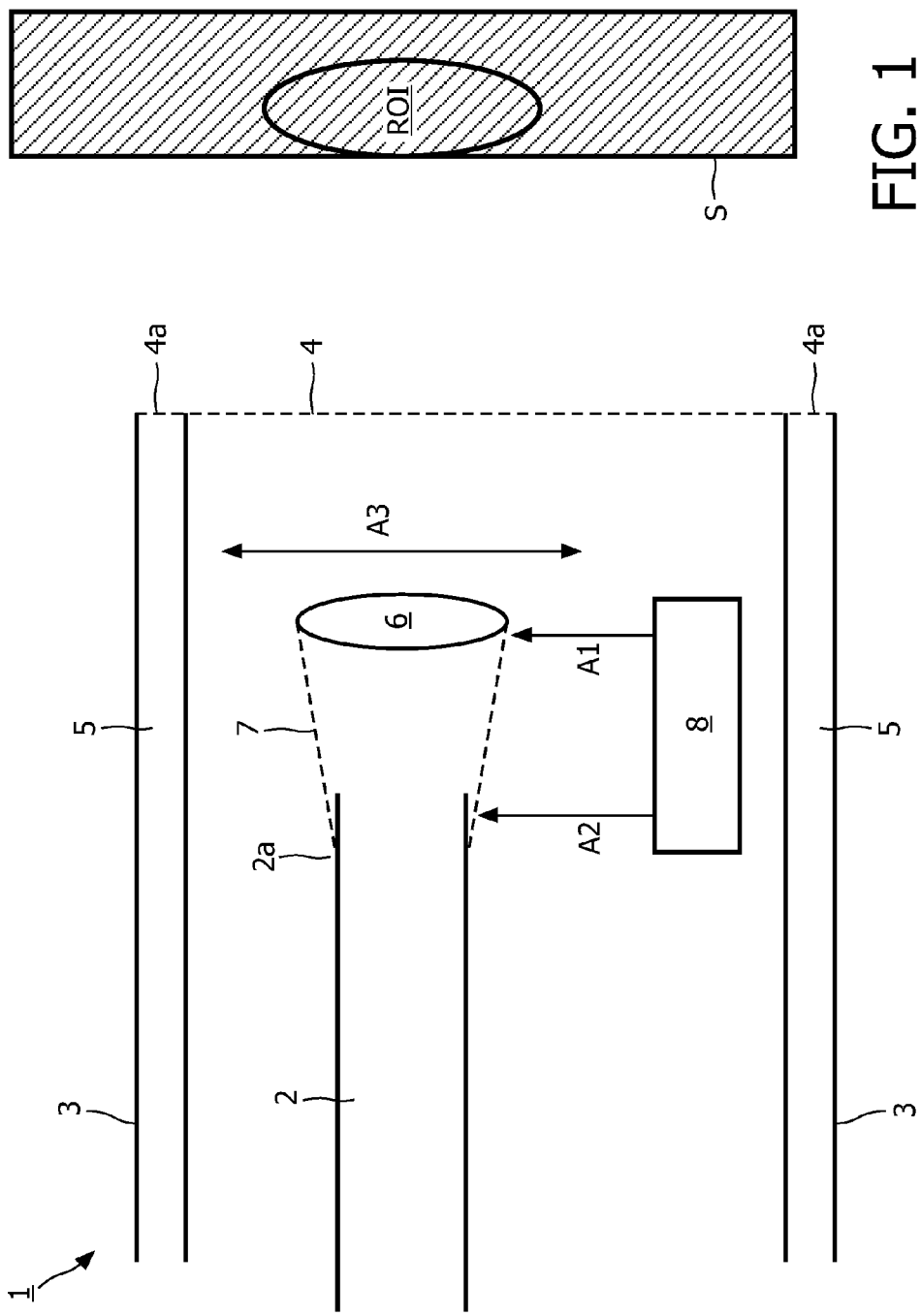
FIG. 1 is a schematic cross-sectional drawing of an optical image probe according to the present invention.

FIG. 1 is a schematic cross-sectional drawing of an optical image probe 1 according to the present invention for performing imaging in a region of interest (ROI) in a sample S as indicated on the right hand side of FIG. 1. The optical probe 1 comprises an optical guide 2, e.g. an optical fiber, and a housing 3 having a cavity wherein the optical guide 1 can be embedded. The housing 3 has at its distal or sampling end a transparent and substantially non-focusing window 4. The window 4 can be a plane section of an optical transport glass or polymer. The window 4 is preferably non-focusing i.e. it has no optical power, but it is contemplated that the window 4 may for some applications have some focusing effect. This is however not usually the case because it may influence the performance of the lens system 6. It is nevertheless contemplated that the exit window 4 in some cases may be a field flattener lens to make the image plain flat and not curved and this requires a small amount of optical power.

The housing 3 further comprises an auxiliary, peripheral optical guide 5, which can embedded within the housing, or positioned on or adjacent to the inner or outer surface of the housing 3. For collection of light the guide or fiber 2 can be applied in a confocal setup for imaging of the ROI, but there is also an additional collection light path through the guide 5 which is outside the confocal light path collecting photons generated by a two-photon process in front of the probe 1. The additional light path makes use of the outer part of the window 4a that is not used for forming the focus of an excitation beam, cf. FIG. 3 below. The probe 1 may have the distal end of the auxiliary, peripheral optical guide 5 positioned substantially adjacent to the transparent window 4 i.e. facing the window as indicated in FIG. 1. This outer part 4a of the transparent window, which is optically connected to the auxiliary, peripheral optical guide 5, is substantially unused during light emission from the optical probe 1. Thus for confocal imaging the outer part 4a of the window is not used.

A lens system 6 is rigidly coupled to an end portion 2a of the optical guide 2. The lens system 6 is merely for reason of clarity in the Figure shown as a single lens. As will be evident below, the lens system 6 may also have more than one lens and also may contain diffractive elements or mirror elements. The coupling between the lens system 6 and the optical guide 2 is preferably mechanical i.e. there is an intermediate mount 7 keeping the position of the lens system 6 and the optical exit of the optical guide 2 in a fixed position relative to each other.

Actuation means 8 that are capable of displacing the lens system 6 is also provided. The actuation means 8 may be more or less directly actuating on the lens system 6 as indicated by arrow A1. In practical implementation, the actuation means 8 is most likely to be mechanical contact with the mount 7. Alternatively or additionally, the actuation means 8 may be indirectly actuating the lens system 6 via the end portion 2a of the optical guide 2 as indicated by arrow A2. The function of the actuation means 8 is that the actuation means 8 is arranged for displacing the lens system 6 so as to enable optical scanning of a region of interest ROI outside the window 4. Typically, the optical guide 2 is made in a flexible material so as to facilitate inspection on not easy accessible positions, e.g. in-vivo medical inspection and/or sample taking, and in that case the optical guide 2 may be fixated or resting at a point some distance away from the end portion 2a making it possible to elastically displace at least part of the optical guide 2 by the actuation means 8. Various solutions for displacement of an optical guide 2 at an end of a probe are discussed in US2001/0055462, which is hereby incorporated by reference in its entirety.

In order to obtain a compact optical probe 1, lens system 6 preferably comprises an aspherical lens thereby making it possible to have a relative high numerical (NA), e.g. a numerical aperture above 0.3, 0.4, or 0.5 or even higher.

Figure 2:
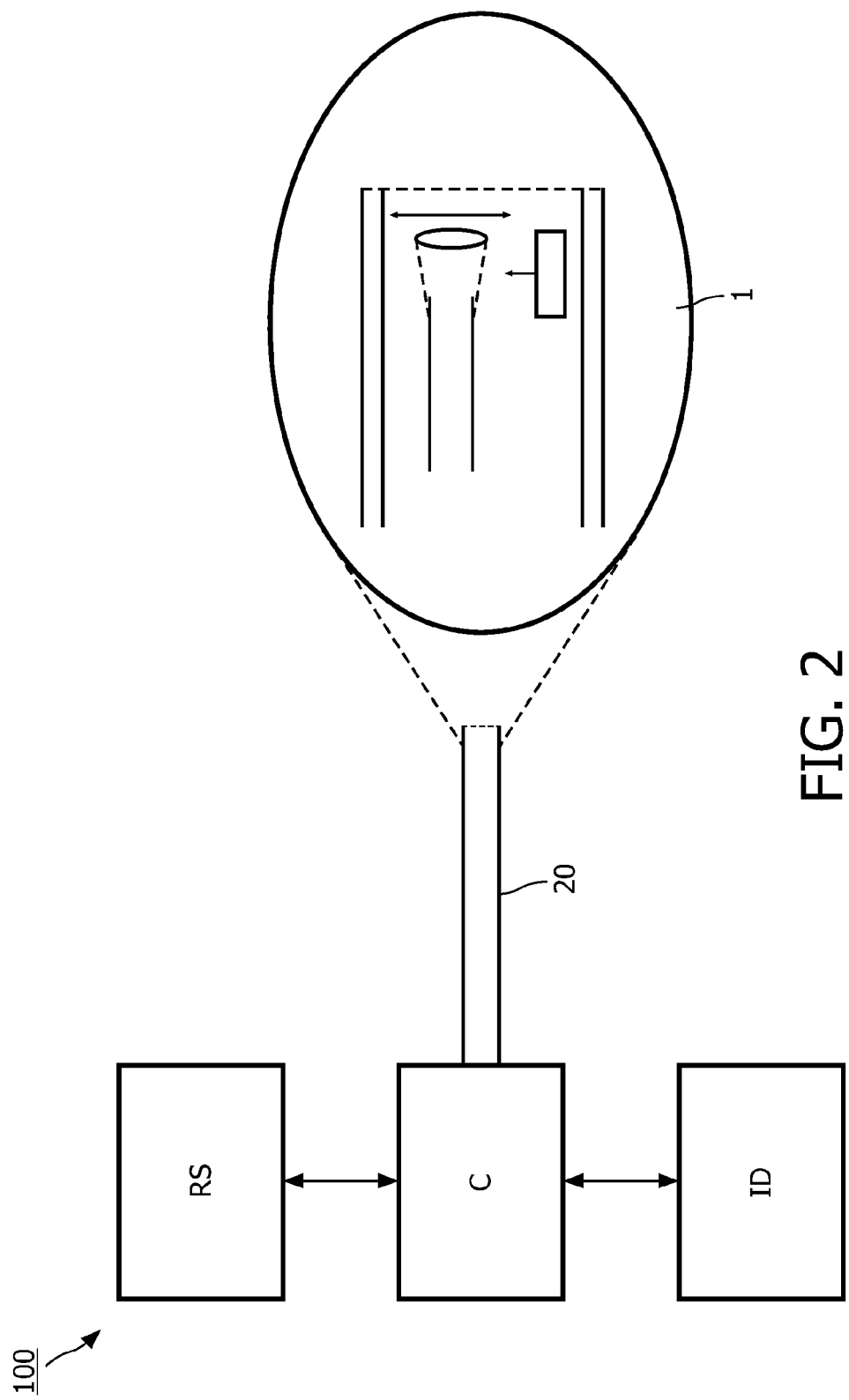
FIG. 2 is a schematic drawing of an optical imaging system according to the present invention.

FIG. 2 is a schematic drawing of an optical imaging system 100 according to the present invention. The optical imaging system comprises an optical probe 1 as described above at an end portion of a sample arm 20. The sample arm 20 preferably being highly flexible, and it is possible bendable to some extent. The optical probe 1 is shown the magnified portion and is similarly to FIG. 1.

Additionally, a radiation source RS is optically coupled to the optical probe 1 via a coupler C. The probe 1 is accordingly arranged for guiding radiation, e.g. laser light, emitted from the radiation source RS to a region of interest ROI, and furthermore an imaging detector ID is optically coupled to the optical probe 1. The imaging detector is arranged for imaging using reflected radiation from the region of interest ROI in the sample (not shown). The imaging detector ID may also comprise a user interface (UI) for accessing results and/or controlling the imaging process.

Figure 3A:
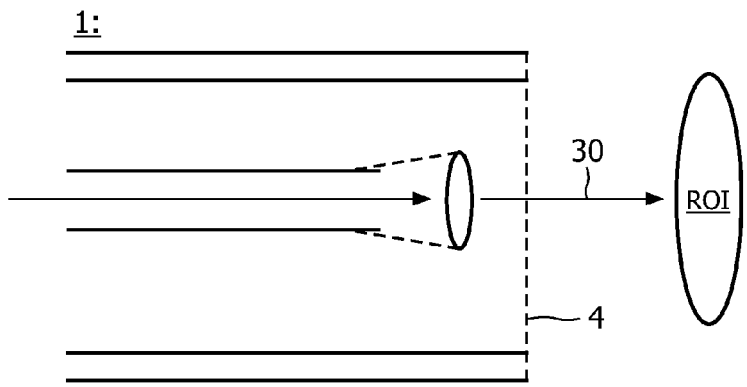
FIG. 3 shows a schematic drawing of the optical path for an optical probe imaging a region of interest (ROI) according to the present invention.
Figure 3B:
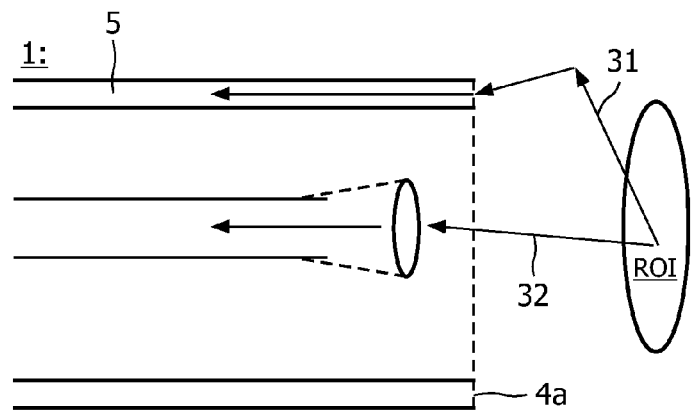

FIG. 3 shows a schematic drawing of the optical path for an optical probe imaging a region of interest ROI according to the present invention.

In the upper part A of FIG. 3, an emitted beam 30 from the probe 1 is focused in a focal point within the ROI desired for imaging. For instance this could be a suspected malignant tissue part within a patient during an in vivo inspection.

In the lower part B of FIG. 3, two possible optical return paths are shown. In the path 32, the photons produced by a two-photon process can reach the scanning fiber 2 via the same return optical path 30 using the lens 6, so-called ballistic photons. Another part of the produced photons becomes scattered, so-called diffusive photons, and cannot reach the scanning fiber 2 tip anymore. Part of these scattered photons are now collected according to the invention by the outer part 4a of the window, and guided into the auxiliary optical wave guide 5. Thus, the probe according to the present invention significantly increases the collection efficiency, in particular in connection with imaging techniques such as two-photon imaging, where both diffusive and ballistic photons can be used for imaging. This is different from confocal imaging where only ballistic photons passing through the discriminative pin-hole is applied for imaging purposes.

Figure 4:
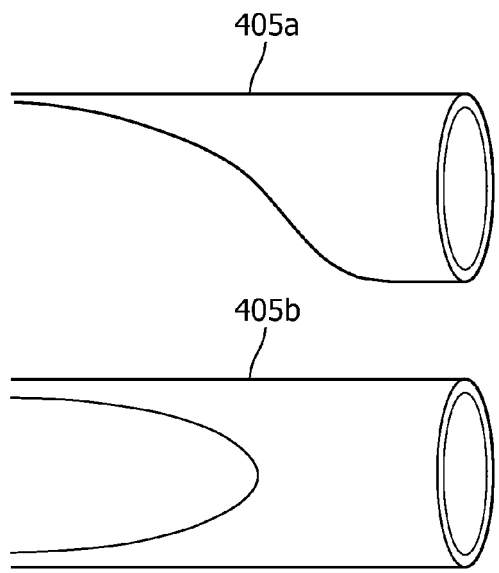
FIG. 4 shows schematic drawings of two auxiliary, peripheral optical guides of an optical probe,
   FIG. 5 show a schematic drawing of an auxiliary, peripheral optical guide changing shape.

FIG. 4 shows schematic drawings of two auxiliary, peripheral optical guides of an optical probe having various shapes. In example 405a, the initial annular shaped optical wave guide at the distal end ends in one rectangular shaped optical wave guide that is connected to a detector ID at the proximal end. In example 405b, the light guide ends in two rectangular shaped optical wave guides to improve the light collection. In order to keep the collection numerical aperture at the distal end large, the area covered by the annular ring at the distal end should be comparable in size compared to the area covered by the rectangular shaped proximal end. This is due to conservation of etendue as it will be understood by the person skilled in optics. For more details on these tapered fibers the catalog of Polymicro, Phoenix, Ariz., USA, may be consulted.

In FIG. 4, the peripheral optical guide 405a or 405b is shown as one entity, but the peripheral optical guide may comprise a plurality of elements optically connected to form a coherent optical guide peripherally positioned around the central optical guide 2, cf. FIG. 1.

Figure 5:
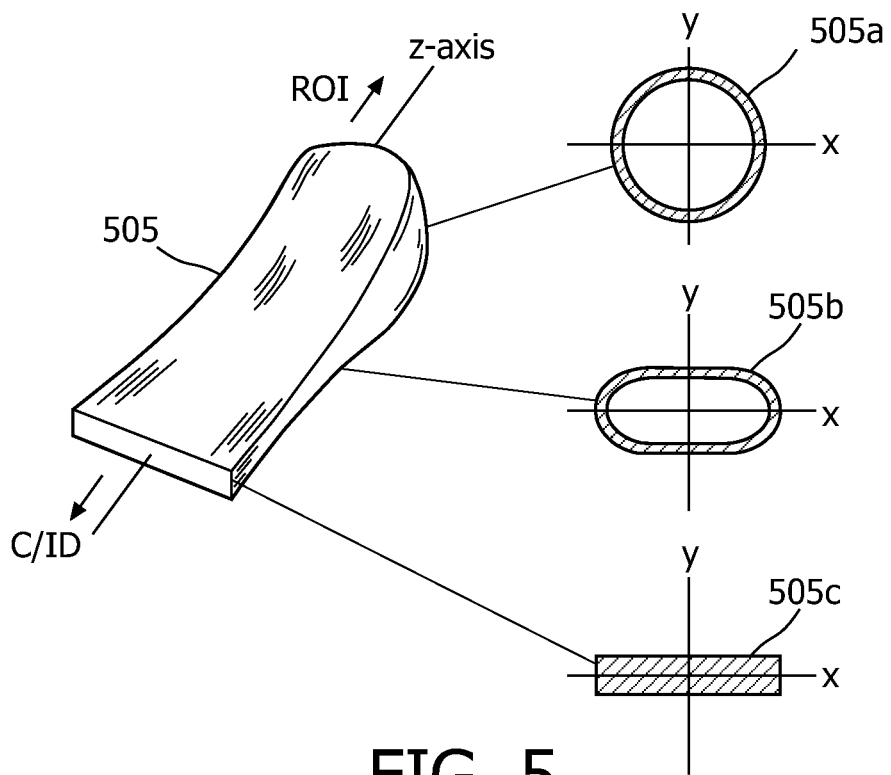

FIG. 5 shows a schematic drawing of an auxiliary, peripheral optical guide changing shape from an annular shape to a rectangular shape. The area of the annulus and the rectangle are comparable. The rectangular shape is suitable to be connected to the entrance slit of the spectrograph in the image detector ID (not shown in this Figure, see FIG. 2). In coordinate systems 505a, 505b, and 505c various cross-sections are shown of the changing shape of the optical guide 505.

Figure 6:
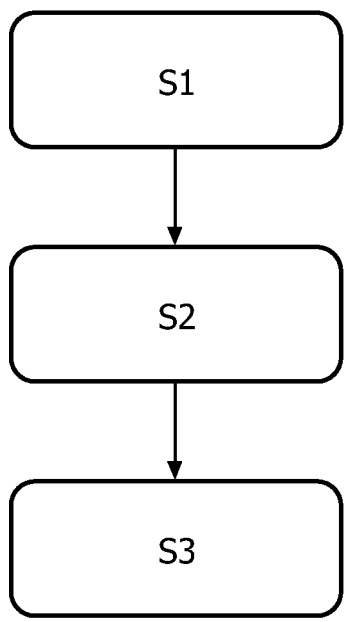
FIG. 6 is a flow chart for a method according to the invention.

FIG. 6 is a flow chart for a method according to the invention. The method comprises:

S1 providing an optical probe 1, cf. FIG. 1,

S2 providing a radiation source RS which is optically coupled through C to said optical probe 1, the probe being arranged for guiding radiation emitted from the radiation source to a region of interest ROI, and S3 performing an imaging process with an imaging detector ID optically coupled to the optical probe 1, the detector being arranged for imaging using reflected radiation from the region of interest ROI.

The invention can be implemented in any suitable form including hardware, software, firmware or any combination of these. The invention or some features of the invention can be implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. An optical probe (1), the probe comprising:
   an optical guide (2),
   a lens system (6) positioned rigidly at a distal end portion (2a) of the optical guide,
   a housing (3) with a cavity for the optical guide (2) and the lens system (6), the housing having at its distal end a transparent window (4),
   wherein the optical guide (2) with the lens system (6) is displaceably mounted within the housing, and
   wherein the housing (3) further comprises an auxiliary, peripheral optical guide (5) optically connecting the transparent window (4) to an image detector (ID).

2. The optical probe according to claim 1, wherein the optical guide (2) and the lens system (6) is arranged for confocal imaging.

3. The optical probe according to claim 2, wherein the auxiliary, peripheral optical guide (5) is arranged for non-confocal imaging.

4. The probe according to claim 1, wherein the auxiliary, peripheral optical guide (5) is arranged for receiving reflected light emitted by the optical probe.

5. The probe according to claim 1, wherein the auxiliary, peripheral optical guide (5) extends substantially along at least half the periphery of the end part of the optical probe.

6. The probe according to claim 1, wherein the optical guide (2) is an optical fiber, the lens system (6) being positioned a distance (L) away from the optical exit of the optical fiber, the distance (L) being significantly larger than a core diameter ($D_f$) of the optical fiber.

7. The probe according to claim 1, wherein the lens system (6) is rigidly connected to the optical guide with an intermediate mount fixated at the distal end (2a) of the optical guide and fixated on the lens system (6).

8. The probe according to claim 7, wherein the lens system (6) mounted at the distal end (2a) of the optical guide is mounted displaceable in a transverse direction (A3) of the optical guide (2).

9. The probe according to claim 1, wherein the transparent windows (4) comprises a further lens system, the further lens system being rigidly connected to the housing (3).

10. The probe according to claim 1, wherein the lens system (130) has a numerical aperture so as to enable non-linear optical phenomena.

11. The probe according to claim 1, wherein the optical guide is a photonic crystal fiber, or a polarization maintaining fiber.

12. An optical imaging system (100), the system comprising
   an optical probe (1) according to claim 1,
   a radiation source (RS) optically coupled to said optical probe (1), the probe being arranged for guiding radiation emitted from the radiation source to a region of interest (ROI), and
   an imaging detector (ID) optically coupled to said optical probe (1), the detector being arranged for imaging using reflected radiation from the region of interest (ROI).

13. The optical imaging system according to claim 12, wherein the radiation source (RS) of the optical imaging system is capable of emitting radiation with an intensity, and/or with a spatial and temporal distribution so at to enable non-linear optical phenomena.

14. The optical imaging system according to claim 12, the system being a two photon imaging system, a second or third harmonic generation (SHG) imaging system, or a fluorescence imaging system.

15. A method for optical imaging, the method comprising:
   providing an optical probe (1) according to claim 1,
   providing a radiation source (RS) which is optically coupled to said optical probe, the probe being arranged for guiding radiation emitted from the radiation source to a region of interest (ROI), and
   performing an imaging process with an imaging detector (ID) optically coupled to said optical probe, the detector being arranged for imaging using reflected radiation from the region of interest (ROI).

16. The optical probe according to claim 1, wherein the optical guide (2) and the auxiliary, peripheral optical guide (5) are configured to provide two separate return paths for light reflected from a region of interest.

* * * * *